United States Patent
Matsui et al.

(10) Patent No.: US 7,834,139 B2
(45) Date of Patent: Nov. 16, 2010

(54) MAGNETIC NANOTUBES

(75) Inventors: Hiroshi Matsui, Glen Rock, NJ (US); Tadashi Matsunaga, Tokyo (JP)

(73) Assignees: Research Foundation of the City University of New York, New York, NY (US); National University Corporation of Tokyo University of Agriculture and Technology, Tokyo (JP)

( * ) Notice: Subject to any disclaimer, the term of this patent is extended or adjusted under 35 U.S.C. 154(b) by 225 days.

(21) Appl. No.: 10/593,514

(22) PCT Filed: Mar. 14, 2005

(86) PCT No.: PCT/US2005/007953
§ 371 (c)(1),
(2), (4) Date: Apr. 9, 2007

(87) PCT Pub. No.: WO2005/108302
PCT Pub. Date: Nov. 17, 2005

(65) Prior Publication Data
US 2007/0200085 A1    Aug. 30, 2007

(51) Int. Cl.
*A61K 38/00* (2006.01)
*H01F 1/00* (2006.01)
*C01G 49/08* (2006.01)

(52) U.S. Cl. ............. 530/300; 977/838; 977/904; 252/62.51 R; 252/62.56

(58) Field of Classification Search .......... None
See application file for complete search history.

(56) References Cited

U.S. PATENT DOCUMENTS 6,975,063 B2 *  12/2005  Mao et al. ............ 313/309
7,504,383 B2 *  3/2009   Gazit et al. ............ 514/19
2004/0166152 A1  8/2004   Hirsch et al.
2007/0276131 A1 * 11/2007  Ferre et al. ............ 530/420

FOREIGN PATENT DOCUMENTS

WO   WO 2005019263 A1 *  3/2005

OTHER PUBLICATIONS

Lee et al. (Feb. 2004; Other Condensed Matter: http://arxiv.org/abs/cond-mat/0402204).*

* cited by examiner

*Primary Examiner*—Janet L Epps-Smith
(74) *Attorney, Agent, or Firm*—Hoffmann & Baron, LLP; Irving N. Feit

(57) ABSTRACT

A magnetic nanotube includes bacterial magnetic nanocrystals contacted onto a nanotube which absorbs the nanocrystals. The nanocrystals are contacted on at least one surface of the nanotube. A method of fabricating a magnetic nanotube includes synthesizing the bacterial magnetic nanocrystals, which have an outer layer of proteins. A nanotube provided is capable of absorbing the nanocrystals and contacting the nanotube with the nanocrystals. The nanotube is preferably a peptide bolaamphiphile. A nanotube solution and a nanocrystal solution including a buffer and a concentration of nanocrystals are mixed. The concentration of nanocrystals is optimized, resulting in a nanocrystal to nanotube ratio for which bacterial magnetic nanocrystals are immobilized on at least one surface of the nanotubes. The ratio controls whether the nanocrystals bind only to the interior or to the exterior surfaces of the nanotubes. Uses include cell manipulation and separation, biological assay, enzyme recovery, and biosensors.

25 Claims, 3 Drawing Sheets

MAGNETIC NANOTUBES

This invention was made with support from the U.S. Government under Contract No. DE-FG-02-01ER45935 awarded by the Department of Energy. The U.S. Government has certain rights in the invention.

FIELD OF THE INVENTION

The invention relates to the field of nano-scale magnetic structures, and more particularly to magnetic nanotubes and methods of fabricating the same.

BACKGROUND OF THE INVENTION

Recently emerging technologies in recording media, spintronics, imaging, and sensors, have driven a need for nanometer-scale magnetic materials and devices and methods for making them. Nanometer-scale magnetic building blocks are typically used to fabricate such magnetic nanostructures. Recently, considerable efforts have been made in the area of self-assembling magnetic nanostructures. For example, three-dimensional assemblies of magnetic nanocrystals have been extensively investigated in order to apply them as building blocks in magnetic devices, where the control of the size, shape, and morphology of the nanocrystals is critical for the suitable catalytic, optical, and magnetic properties. One of the important classes of building block structures is a magnetic nanowire. Synthetic magnetic nanowires have been produced; however, the ability to tune the magnetic properties of these nanowires has proven to be difficult.

In addition, magnetic particles are used commercially for cell separation. Typical commercial magnetic particles are paramagnetic, however, and on the order of micrometers in diameter. Smaller magnetic particles are desired for applications such as biosensors, magnetic separation, biological assays, and enzyme substrate. The use of smaller particles increases the efficiency of cell separation, for example, due simply to the resultant increased surface area. The synthetic manufacture of the desired nanometer-sized magnetic particles for these applications is difficult, however, because such tiny particles are extremely difficult to collect, even with the use of magnetic fields, due to their characteristically weak magnetic moments.

There exists a need, therefore, which is lacking, in the prior art, for magnetic nanometer-sized particles and nanotubes of greater magnetic field strength than currently available. There also exists a need for new methods of fabricating magnetic nanotubes, which allow for tunability of their magnetic properties.

SUMMARY OF THE INVENTION

A method of fabricating a magnetic nanotube includes the step of providing bacterial magnetic nanocrystals, where each of the bacterial magnetic nanocrystals has an outer layer. The method further includes providing at least one nanotube, which is capable of absorbing the bacterial magnetic nanocrystals, and which has an interior surface and an exterior surface. The method further includes contacting the nanotube with bacterial magnetic nanocrystals.

Preferably, the method further includes the steps of forming a nanotube solution which includes the at least one nanotube, and forming a nanocrystal solution which includes a buffer and a concentration of bacterial magnetic nanocrystals. The concentration of the bacterial magnetic nanocrystals in the nanocrystal solution is optimized, and the nanocrystal solution is mixed and incubated with the nanotube solution until at least a portion of the bacterial magnetic nanocrystals are substantially immobilized on at least one surface of the at least one nanotube.

An optimal concentration depends on whether the magnetic nanotubes are to be contacted substantially on only the interior surface or substantially on at least the exterior surface of the at least one nanotube. One embodiment of the method, therefore, includes selectively incorporating the bacterial magnetic nanocrystals on the interior surfaces of the nanotubes, by diluting the concentration of nanocrystals to the optimal concentration for which the bacterial magnetic nanocrystals are substantially only incorporated on the interior surfaces of the nanotubes.

A magnetic nanotube includes bacterial magnetic nanocrystals, each of which has an outer layer, and a nanotube with an interior and an exterior surface, which is capable of absorbing the bacterial magnetic nanocrystals. The bacterial magnetic nanocrystals are contacted on at least one of the interior and exterior surface of the nanotube.

The outer layer of the bacterial magnetic nanocrystals preferably comprises proteins.

In one embodiment, the bacterial magnetic nanocrystals are contacted substantially on the interior surface of the nanotube, and are aligned to form a linear chain on the interior surface of the nanotube.

The magnetic nanotube may be adapted for use as a magnetic nanowire and for cell manipulation. The magnetic nanotube may further be adapted for use in a cell separation system, a biological assay system, and an enzyme recovery system. The magnetic tube may further be adapted for use in drug and gene delivery systems. The magnetic nanotube may also be adapted for use in magnetic resonance imaging.

DETAILED DESCRIPTION

Figure 1:
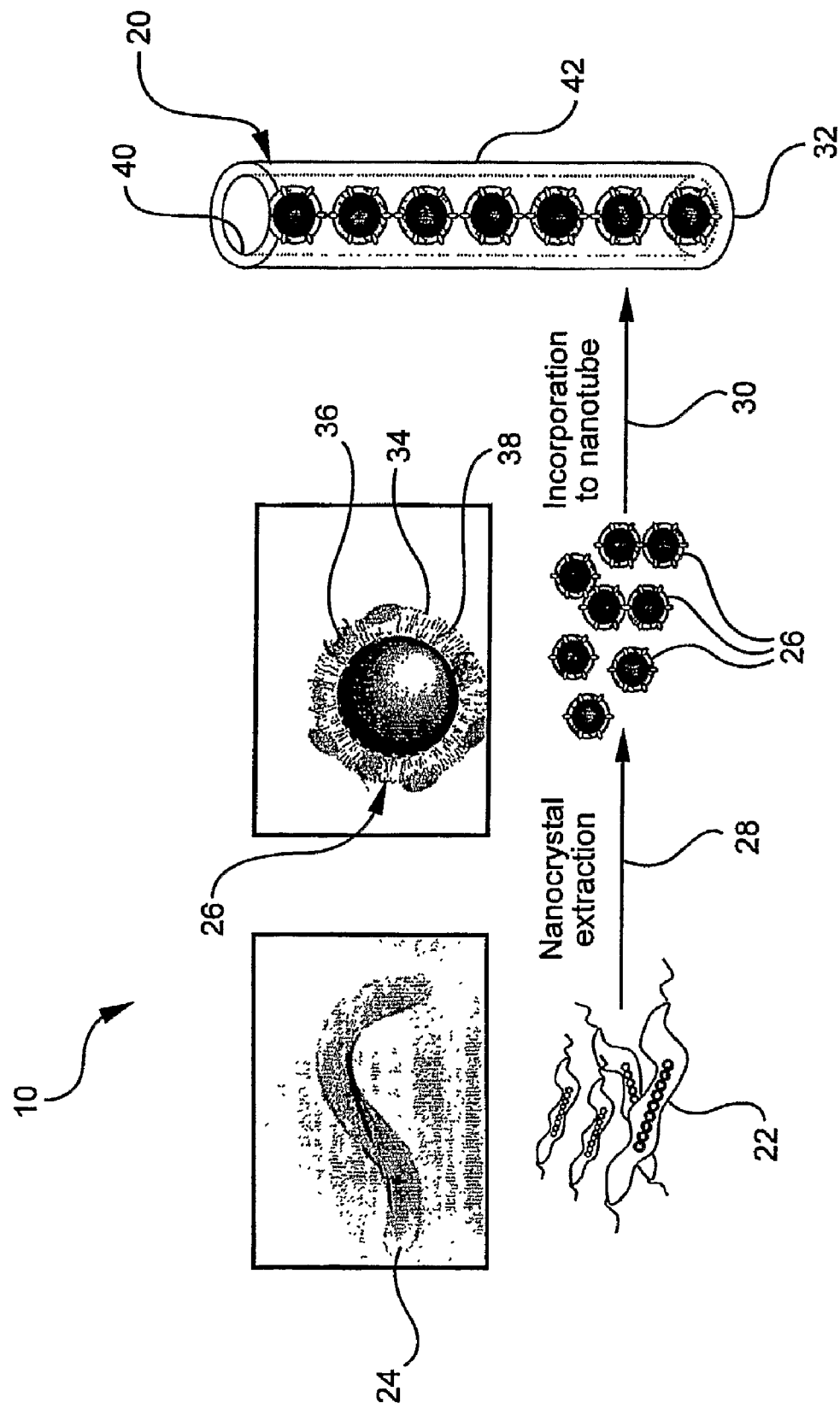
FIG. 1 is a pictorial representation of a method for fabricating a magnetic nanotube in accordance with the present invention.

FIG. 1 is a pictorial representation of an embodiment of a method 10 for fabricating a magnetic nanotube in accordance with the present invention, and a pictorial view of one embodiment of the magnetic nanotube 20 formed in accordance with the present invention. In one step, bacterial magnetic nanocrystals 26 are provided. In the embodiment shown in FIG. 1, the step of providing the bacterial magnetic nanocrystals 26 includes the step 22 of synthesizing the nanocrystals 26 by growing at least one bacterium 24 anaerobically and an additional step 28 in which the magnetic nanocrystals 26 are extracted from the bacterium 24. In step 30, the magnetic nanocrystals 26 are contacted on at least one surface of a nanotube 32 to form one embodiment of the magnetic nanotube 20 of the present invention.

The step 30 of contacting includes distributing nanocrystals 26 on at least a portion of one or more surfaces of the nanotube 32. The step 30 of contacting may also include distributing nanocrystals 26 over substantially at least one entire surface, resulting in a substantially uniform coating of one or more surfaces of the nanotube 32 with nanocrystals 26.

As shown in FIG. 1, the magnetic nanotube 20 of the present invention comprises a plurality of bacterial magnetic nanocrystals 26. Each of the bacterial magnetic nanocrystals 26 comprises an outer layer 34, which preferably includes proteins 36. The outer layer 34 may also include lipids 38. The magnetic nanotube also comprises the nanotube 32, which has an interior surface 40 and an exterior surface 42.

The step 30 of contacting includes distributing nanocrystals 26 on at least a portion of one or more surfaces of the nanotube 32. The step of contacting may also include distributing nanocrystals 26 over substantially at least one entire surface, resulting in a substantially uniform coating of one or more surfaces of the nanotube 32 with nanocrystals.

A plurality of bacterial magnetic nanocrystals 26 may be at least the number of nanocrystals 26 required to partially cover at least a portion of one or more surfaces of the nanotube 32. The plurality of bacterial magnetic nanocrystals 26 may also be at least the number of nanocrystals 26 required to substantially cover at least one entire surface of the nanotube 32. The plurality of bacterial magnetic nanocrystals 26 may also be the number of nanocrystals 26 required to mix with a number of nanotubes 32 to substantially cover at least a portion of one or more surfaces of the number of nanotubes 32.

The nanotube 32 is tubular in shape, having a substantially circular cross-section, a length substantially greater than a diameter of the circular cross-section, and being open-ended on at least one end of the tubular length. The nanotube 32 is characterized by an ability to absorb the bacterial magnetic nanocrystals 26. Preferably, the nanotube 32 absorbs the outer layer 34, which preferably includes protein 36.

In one embodiment, the nanotube 32 includes an inner diameter of at least about 30 nanometers (nm).

In another embodiment, the nanotube 32 includes an inner diameter of less than about 150 nm.

In a preferred embodiment, the nanotube 32 includes an inner diameter substantially in a range of about 45 nm to about 125 nm.

The length of the nanotube 32 is preferably at least a factor of about 10 greater than the outer diameter of the circular cross-section.

Figure 2B:
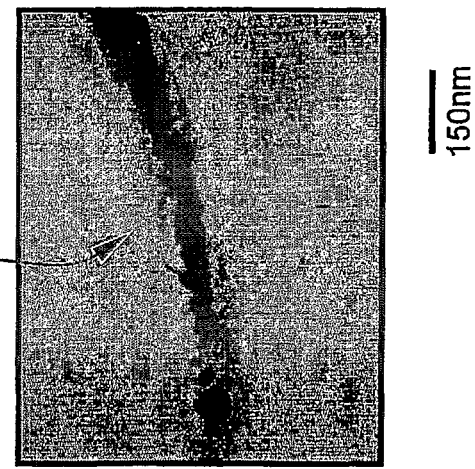
FIG. 2B is a transmission electron micrograph (TEM) of another embodiment of the magnetic nanotube of the present invention, wherein bacterial magnetic nanocrystals are coated substantially on an interior surface only of the peptide nanotube formed in accordance with the present invention. NOTE: Scale bar=150 mm.
Figure 2A:
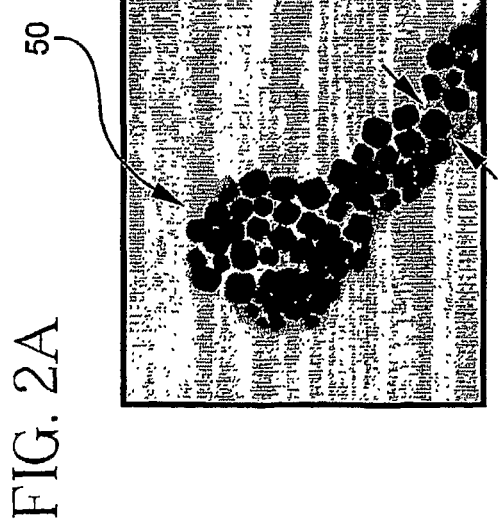
FIG. 2A is a transmission electron micrograph (TEM) of one embodiment of the magnetic nanotube of the present invention, wherein bacterial magnetic nanocrystals are coated on both interior and exterior surfaces of a peptide nanotube formed in accordance with the present invention. NOTE: Scale bar=150 nm.

One embodiment 50 of the magnetic nanotube of the present invention, of which a transmission electron micrograph (TEM) is shown in FIG. 2A, is characterized by the plurality of bacterial magnetic nanotubes 26 being contacted on both the interior 40 and exterior surfaces 42. In another embodiment (not shown), the magnetic nanotube is characterized by bacterial magnetic nanocrystals being contacted substantially on the exterior surface 42 only.

Another embodiment 20 of the magnetic nanotube, shown pictorially in FIG. 1 and in a TEM in FIG. 2B, is characterized by bacterial magnetic nanocrystals 26 being substantially selectively incorporated inside the nanotube 32, the bacterial magnetic nanocrystals 26 being contacted on the interior surface 40 only.

The bacterial magnetic nanocrystals 26 which are selectively incorporated may form a single linear chain down the center of the interior of the nanotube 32, as shown in FIG. 1, in which case, an outer diameter of the nanocrystals 26 is not more than an inner diameter of the nanotube 32.

In an additional embodiment in which the nanocrystals 26 are selectively incorporated in the interior of the nanotube, the outer diameter of the nanocrystals is preferably not less than one-half the diameter of the nanotube 32. In this embodiment, nanocrystals incorporated in the interior preferably contact at least one side of the interior surface 40 of the nanotube 32.

In another embodiment in which the magnetic nanocrystals 26 are selectively incorporated inside the nanotube 32, the inner diameter of the nanotube is preferably substantially the same as the outer nanocrystal diameter, so that nanocrystals incorporated in the interior contact both sides of the interior surface 40 of the nanotube 32.

By controlling various parameters during the fabrication of the magnetic nanotubes, certain magnetic properties of the magnetic nanotubes can be controlled. For example, the nanotube 20, shown in FIG. 1 and FIG. 2B, is preferably fabricated by optimizing a concentration of nanocrystals 26 in a nanotube solution during the contacting step 30 of FIG. 1. This incorporation of the magnetic nanocrystals 26 inside the nanotube 32 results in a linear chain of magnetic particles inside the nanotube 32, which introduces a uniaxial magnetic anisotropy, not present in the magnetic particles or assemblies commonly known.

In addition, the phase, mineral type, crystal size, and morphology of the magnetic nanocrystals of the present invention may be controlled by proper selection of bacterial species or strains. For example, some bacteria produce single-domain magnetic nanocrystals in ambient conditions. Such nanocrystals are difficult to fabricate by synthetic means. Therefore, parameters of the method of the present invention may advantageously be adjusted to produce magnetic nanotubes having specific magnetic properties, by controlling the morphology and location of magnetic nanocrystals on the nanotubes.

Referring again to FIG. 1, the nanotube 32 of the present invention comprises biological material capable of absorbing the nanocrystals 26. Preferably the nanotube 32 is capable of absorbing the outer layer 34, which preferably includes proteins 36.

The nanotube 32 is preferably produced by self-assembly of a peptide bolaamphiphile molecule, as described, for example, in Matsui, H., et al., "Crystalline Glycylglycine Bolaamphiphile Tubules and their pH Sensitive Structural Transformation," *J. Phys. Chem. B.* 104, 3383-3386 (2000), which is incorporated herein by reference.

The peptide bolaamphiphile molecule of the present invention is any molecule comprising two polar heads or groups connected with a non-polar chain. Each of the two polar groups may be any functional group that can bind to a peptide or to a protein using hydrogen bonding. Some examples of functional groups of the nanotube 32 of the present invention include those selected from the group consisting of an amide group, a hydroxyl group, and a carboxylate group. The two polar groups on a chain may be the same or different.

Examples of peptide bolaamphiphiles include: bis(N-alpha-amido-glycylglycylglycine)-1,6-hexane dicarboxylate, bis(N-alpha-glycylglycine)-1,6-hexane dicarboxylate, bis(N-alpha-amido-glycylglycine)-1,7-heptane dicarboxylate, bis(N-alpha-glycylglycine)-1,8-octane dicarboxylate, bis(N-alpha-glycylglycine)-1,9-nonane dicarboxylate, bis(N-alpha-glycylglycine)-1,10-decane, dicarboxylate, bis(N-alpha-glycylglycine)-1,11-undecane dicarboxylate, bis(N-alpha-glycylglycine)-1,12-dodecane dicarboxylate, bis(N- alpha-glycylglycine)-1,14-tetradecane dicarboxylate, bis(N-alpha-glycylsarcosylsarcosine)-1,10-decane dicarboxylate, and bis(N-alpha-glycyl-L-prolyl-L-proline)-1,10-decane dicarboxylate.

In a preferred embodiment, the nanotube template is self-assembled from a dicarboxylic oligopeptide bolaamphiphile comprising amide functional groups. A most preferred nanotube of the present invention comprises bis(N-alpha-amido-glycylglycine)-1,7-heptane dicarboxylate.

The peptide nanotube assembly comprises intermolecular hydrogen bonds between the functional groups (amide, hydroxyl, and/or carboxylic) of the bolaamphiphile peptide molecule. Each bolaamphiphile peptide molecule contains at least one free amide site in the tubule assembly. Proteins preferably interact with the tubule free amide sites via hydrogen bonds to produce uniform coatings on the peptide nanotube.

The peptide nanotubes of the present invention are capable of anchoring various types of proteins, as well as enzymes, other peptides, and antibodies on the nanotube surfaces. The proteins on the bacterial magnetic nanocrystals of the present invention have demonstrated a particularly strong affinity toward the peptide nanotubes. This affinity facilitates the contacting of the bacterial magnetic nanocrystals onto the surfaces of the peptide nanotubes.

Referring again to FIG. 1, the bacteria 24 of the present invention include any so-called "magnetic bacteria" that produce magnetic nanocrystals. Commonly known magnetic bacteria synthesize intracellular membrane bound magnetic particles 26 of either an iron oxide, magnetite ($Fe_3O_4$), or iron sulfide, greigite ($Fe_3S_4$). Formation of this structure by the bacteria 24 is achieved by a mineralization process with control over the accumulation of iron and the deposition of the mineral particle in the cell. The preferred strains of magnetic bacteria of the present invention are preferably anaerobic and capable of being axenically cultivated under laboratory conditions. The preferred strains include *Magnetospirillum magnetotacticum* MS-1, *Magnetospirillum gryphiswaldense*, and *Magnetospirillum magneticum* AMB-1.

The magnetic nanocrystals 26 of the present invention include any substantially crystalline, substantially magnetic material produced by bacteria. Preferably, the magnetic nanocrystals 26 comprise magnetite ($Fe_3O_4$) or greigite ($Fe_3S_4$). The magnetic nanocrystals 26 are also preferably substantially spherical in shape.

In one embodiment, the magnetic nanocrystals are of average diameter less than about 500 nanometers (nm).

In another embodiment, the magnetic nanocrystals include a diameter of about 40 nm or more.

In a preferred embodiment, the diameter of the magnetic nanocrystals are substantially in a range of about 40 nm to about 60 mm.

In another embodiment, the diameter of the magnetic nanocrystals are substantially in a range of about 50 nm to about 100 nm.

The magnetic nanocrystals 26 of the present invention also preferably comprise an outer layer or membrane 34, which comprises a protein 36. Typically, the outer layer 34 comprises a stable bilayer membrane, which includes both lipids 38 and proteins 36. The proteins 36 produced by the magnetic bacteria have been characterized in Wahyudi, et al., "Characterization of Aldehyde Ferredoxin Oxidoreductase Gene Defective Mutant in *Magnetospirillum magneticum* AMB-1," *Biochemistry & Biophysics Research Comm.* 303, 223-229 (2003), which is incorporated herein by reference.

The preferred magnetic nanotubes formed in accordance with the method of the present invention are ferromagnetic and possess an unusually strong magnetic moment due to the alignment of bacterial magnetic nanocrystals in the nanotube cavity along the crystalline axis. The magnetic fields exerted by the magnetic nanotubes of the present invention can be several orders of magnitude greater than commercially available magnetic nanoparticles, presently used for cell separation.

Referring to the method described pictorially in FIG. 1, in step 22, bacteria 24 are used to synthesize the magnetic nanocrystals 26. Preferably, this step 22 includes growing the bacteria 24 anaerobically, in a fermentor, for example, as described in Yang, C. D. et al., "Effects of growth Medium Composition, Iron Sources and Atmospheric Oxygen Concentrations on Production of Luciferase-Bacterial Magnetic Particle Complex by a Recombinant *Magnetospirillum Magneticum* AMB-1,", *Enzyme Microb. Technol.* 29, 13-19 (2001), the disclosure of which is incorporated herein by reference.

The step 28 of extracting the nanocrystals 26 from the bacteria 24 may be performed by any method known to those skilled in the art. In one embodiment of the method of the present invention, step 28 includes disrupting harvested cells, collecting the nanocrystals 26 in a column using a magnet, preferably Neodymium-boron (Nd—B), and removing the supernatant comprising the nanocrystals 26, as described in Matsunaga, T., et al., "Chemiluminescence Enzyme Immunoassay using Bacterial Magnetic Particles," *Anal. Chem.* 68, 3551-3554 (1996), the disclosure of which is incorporated herein by reference. The magnetic nanocrystals 26 collected in the supernatant are then preferably washed with a buffer.

In one embodiment, a pH of the buffer is at least pH 5.

Preferably, the pH is about 6 pH.

In another embodiment, the pH of the buffer is not more than about pH 9.

Preferably, the pH is not more than about pH 8.

Most preferably, the pH of the buffer is about pH 7.

Preferably, the buffer is a HEPES buffer.

The step 30 of contacting the nanocrystals 26 on the nanotubes 32 preferably comprises forming a nanocrystal solution, which comprises a concentration of the nanocrystals 26 suspended in the buffer. The step 30 also includes providing a solution of nanotubes, which comprises the nanotubes 32. In a preferred method, the nanotubes 32 comprise peptide nanotubes. The peptide nanotubes may be synthesized by means well known to those skilled in the art, such as those described in Matsui, H., et al.

The step 30 of contacting further includes mixing a quantity of the nanotube solution with a quantity of the nanocrystal solution and providing an incubation time, during which time the bacterial magnetic nanocrystals 26 are substantially immobilized on surfaces of the nanotubes 32.

The particular concentration of nanocrystals 26 in the buffer relative to a number of nanotubes 32 is one parameter of the method of the present invention which is preferably used to control whether the magnetic nanotube will incorporate nanocrystals 26 on both the interior 40 and exterior surfaces 42, on only the interior surface 40, or on only the exterior surface 42. In one embodiment, the step 30 of contacting further includes the step of mixing a nanocrystal solution with a nanotube solution and incubating the mixture.

In one embodiment, the concentration of nanocrystals 26 in the nanocrystal solution is at least about $1 \times 10^{12}$ nanocrystals per milliliter (nanocrystals/ml) and the number of nanotubes 32 in the nanotube solution is about $1.8 \times 10^9$ nanotubes/ml in the mixing step. Equivalently, in this embodiment, a ratio of at least about 550 nanocrystals per nanotube is provided in the mixing step. In this embodiment, bacterial magnetic nanocrystals 26 are contacted substantially on at least the exterior surface 42 of the nanotubes 32.

In another embodiment, the concentration of nanocrystals 26 in the nanocrystal solution is substantially in a range of about $1\times10^{12}$ nanocrystals/ml to about $5\times10^{12}$ nanocrystals/ml and the number of nanotubes 32 in the nanotube solution is about $1.8\times10^9$ nanotubes/ml in the mixing step. Equivalently, in this embodiment, the ratio of nanocrystals to nanotubes is substantially in a range of at least about 550 to about 2800 nanocrystals per nanotube. In this embodiment, bacterial magnetic nanocrystals 26 are contacted substantially on at least the exterior surface 42 of the nanotubes 32.

In a preferred embodiment of the present invention, the nanocrystal solution is optimally diluted in the mixing step to a concentration that results in selective incorporation of the magnetic nanocrystals 26 substantially inside the nanotube 32. The preferable concentration of nanocrystals in the nanocrystal solution is not more than about $1\times10^{11}$ nanocrystals/ml and the number of nanotubes 32 in the nanotube solution is about $1.8\times10^9$ nanotubes/ml in the mixing step. Equivalently, in this embodiment, a ratio of not more than about 56 nanocrystals per nanotube is provided in the mixing step.

In yet another embodiment, the nanocrystal solution is optimally diluted in the mixing step to a concentration that results in selective incorporation of the magnetic nanocrystals 26 substantially inside the nanotube 32. The preferable concentration of nanocrystals in the nanocrystal solution in this embodiment is substantially in a range of about $5\times10^{10}$ to about $1\times10^{11}$ nanocrystals/ml and the number of nanotubes 32 in the nanotube solution is about $1.8\times10^9$ nanotubes/ml in the mixing step. Equivalently, the ratio of nanocrystals to nanotubes is substantially in a range of at least about 27 to about 56 nanocrystals per nanotube in the mixing step.

Ionic strength of the buffer is an additional parameter, which is preferably optimized to selectively incorporate the magnetic nanocrystals 26 substantially inside the nanotube 32. It is believed that this incorporation of bacterial magnetic nanocrystals 26 in the interior of the peptide nanotube takes place via some type of inclusion mechanism, or capillary effect of the nanotubes. The resulting linear chain assembly of nanocrystals 26 produced within the nanotube 32 is able to be magnetostatically coupled; therefore, in this embodiment, the magnetic nanotube 32 behaves as a magnetic nanowire rather than individual particles, and exhibits a higher degree of magnetization.

In another embodiment of the method of the present invention, before the contacting step 30, specific molecules that will bind with the interior surface of the nanotubes 32 are introduced in a solution with the nanotube solution. The modified nanotube solution is then incubated with the nanocrystal solution to form magnetic nanotubes having only the exterior surfaces 42 contacted with the magnetic nanocrystals 26. The specific molecules block the interior binding sites of the nanotubes 32 from binding with the magnetic particles 26.

The unusually strong magnetic moment of the magnetic nanotubes of the present invention enables the collection of these nanometer-sized nanotubes with conventional magnets. Conventional synthetically fabricated magnetic nanotubes do not possess the same magnetic properties and high degree of magnetization as the magnetic nanotubes of the present invention. In addition, the magnetic nanotubes of the present invention are water-soluble, and characterized by unusually high surface areas and excellent dispersion in biological buffers. As a result, these magnetic nanotubes may be used in cell-separation and biological assay systems, offering improvements over conventional systems in separation efficiency, sensitivity, speed of operation, and detection limits.

In addition, the magnetic nanotubes of the present invention may be used to attach to any kind of biological material, including proteins, peptides, enzymes, antibodies, DNA, genes, a virus, bacteria, pathogens, and membranes. They are well-suited, therefore, for use in biological and medical research, e.g. for selective cell manipulation, and for gene delivery.

In one embodiment, specific types of cells of interest may be selectively attached to the nanotubes, and the nanotubes comprising the cells can then be moved with magnetic probes, for example, to separate diseased or cancerous cells from healthy cells. Other potential applications include biosensing, diagnostics, therapeutics, and environmental research.

The magnetic nanotubes of the present invention may further be used to attach to pharmaceuticals, and therefore, may be adapted for use in drug delivery, as well as in gene delivery.

In yet another embodiment, magnetic nanotubes of the present invention may be introduced to desired locations for imaging in the body, and, therefore, used to enhance the contrast in magnetic resonance imaging systems.

In another embodiment, the magnetic nanotubes of the present invention may be used for enzyme recycling. Magnetic nanotubes having magnetic nanocrystals contacted on the exterior surfaces only are preferably used to attach an enzyme onto the interior surfaces, thus protecting the conformation of the enzyme from denaturing. Denaturing is a change in conformation/structure of an enzyme which reduces the enzymatic activity, causing problems particularly in the pharmaceutical industry, because it reduces the yield of chemical products such as drugs. By incorporating enzymes inside the nanotube, therefore, the enzyme conformation or structure is advantageously protected, maximizing the yield of chemical products, including pharmaceuticals.

The magnetic nanotubes of the present invention can be produced, advantageously, for about one tenth of the cost of existing magnetic particles due to the simpler antibody/receptor production and immobilization that can be genetically engineered with bacteria. Furthermore, the genetic engineering of magnetic bacteria offer the advantage of introducing high-valued antibodies and receptors to the magnetic nanotubes of the present invention, which will produce profitable nanotubes for industries.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

Example

The methods described herein have been used to produce magnetic nanotubes in accordance with the present invention. Results of measurements conducted on two embodiments of the magnetic nanotubes produced in accordance with the present invention are also provided.

Among various types of bacteria that produce intercellular magnetite nanocrystals, *Magnetospirillum magneticum* strain AMB-1 was selected as a model to immobilize the extracted bacterial magnetic nanocrystals onto peptide nanotubes. The bacteria were grown anaerobically in an 8-liter fermentor, as described in Yang, C. D. et al.

After harvested cells were disrupted, magnetic nanocrystals were collected from the disrupted cell fraction using a columnar Neodymium-boron (Nd—B), and the supernatant was removed, as described in Matsunaga, T., et al. The collected magnetic nanocrystals were washed 10 times with HEPES buffer at a pH of about 7.0. The purified nanocrystals were suspended in HEPES (1 mg/ml). The *M. magneticum* strain AMB-1 produced $Fe_3O_4$ (magnetite) nanocrystals with an average diameter of 70 nm.

The bacterial magnetic nanocrystals in about pH 7.0 buffer solutions, 100 µL, were mixed with 200 µL of the peptide nanotube solutions. The peptide nanotubes were synthesized by means well known to those skilled in the art, such as described in Matsui, H., et al.

After 48 hrs of incubation at 4° C., the bacterial magnetic nanocrystals were immobilized onto the nanotube surfaces, as shown in FIG. 2A. The bacterial magnetic nanocrystals were coated uniformly on the surfaces of the peptide nanotubes. The bacterial magnetic nanocrystals were aggregated on the peptide nanotubes, as shown in the transmission electron micrograph (TEM) of FIG. 2A, the diameter of the nanocrystal-coated nanotube becoming larger than the diameter of the original nanotube.

By repeating the procedure above, with the exception that the bacterial magnetic nanocrystal solution was diluted by 10 times with a buffer solution and then incubated in the peptide nanotube solution, the contacting of bacterial magnetic nanocrystals was limited to the inside of the peptide nanotubes. In this case, the nanocrystals were aligned as a linear chain, as shown in FIG. 2B. In this condition, 60% of the total number of resulting magnetic nanotubes incorporated the bacterial magnetic nanocrystals inside the nanotubes and the rest (40%) had no magnetic nanocrystals inside.

The magnetic properties of outside- and inside-coated magnetic nanotubes were characterized using a vibrating sample magnetometer (VSM) in an applied magnetic field of flux density $\mu_0 H$ up to 0.5 T at room temperature. As is well-known to those skilled in the art, $\mu_o$ is the magnetic permeability in a vacuum, equal to $$4\pi \times 10^{-7} \frac{WbA}{m},$$

using SI units. The measurement of magnetization, M, in units of A·m, was also carried out in the buffer solution, though no discernible difference was observed between two solvents. The hysteresis loop represented by line 72 in FIG. 3A was obtained from the magnetic nanotube sample with immobilized magnetic nanocrystals at least on the exterior surfaces (shown in FIG. 2A). The coercivity $H_c$ and squareness $M_r/M_s$ values were extracted from the hysteresis loops, where $M_r$ is the remanent magnetization and $M_s$ is the saturation magnetization. The remanent magnetization is represented by the value of the magnetization when no magnetic field is applied, i.e. when $\mu_0 H=0$ (measured in Tesla in the plots of FIG. 3A and FIG. 3B), and is best seen in FIG. 3B, which is a magnification around the center of the plot shown in FIG. 3A. The coercivity $H_c$, a measure of the resistance of the magnetic nanotubes to a reversal of the applied magnetis field, is also best seen in FIG. 3B, and corresponds to the value of $\mu_0 H$ at which the measured net magnetization M is zero, i.e. where $M/M_s=0$. As best shown by FIG. 3B, this embodiment of the magnetic nanotube of the present invention is fairly ferromagnetic with $H_c=5.4$ mT and $M_r/M_s=0.10$.

Figure 3A:
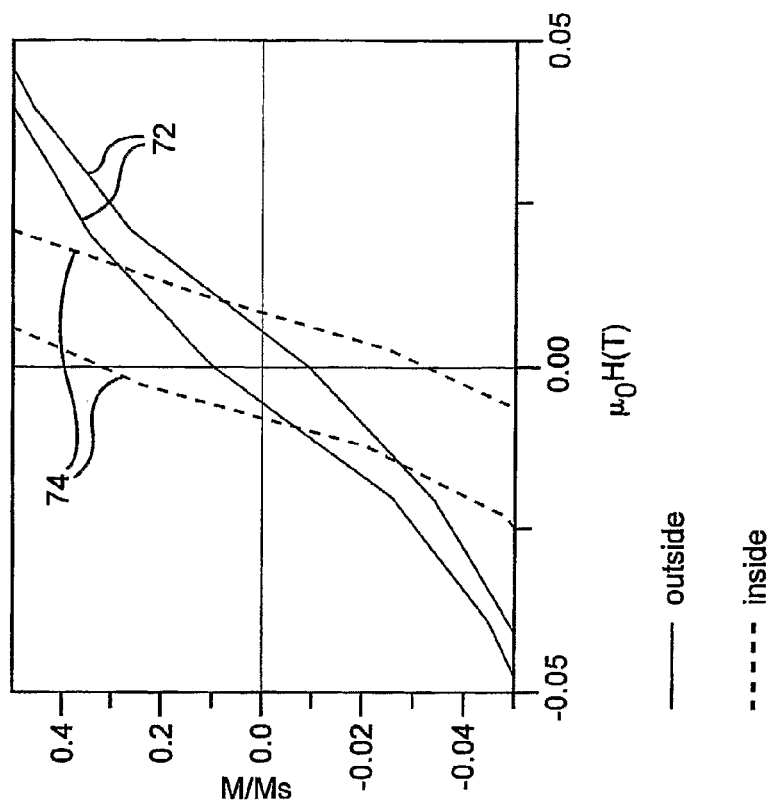
FIG. 3A is a plot of hysterisis curves comparing magnetic properties of nanotubes formed in accordance with the embodiment of FIG. 2A with those of nanotubes formed in accordance with the embodiment of FIG. 2B.
Figure 3B:
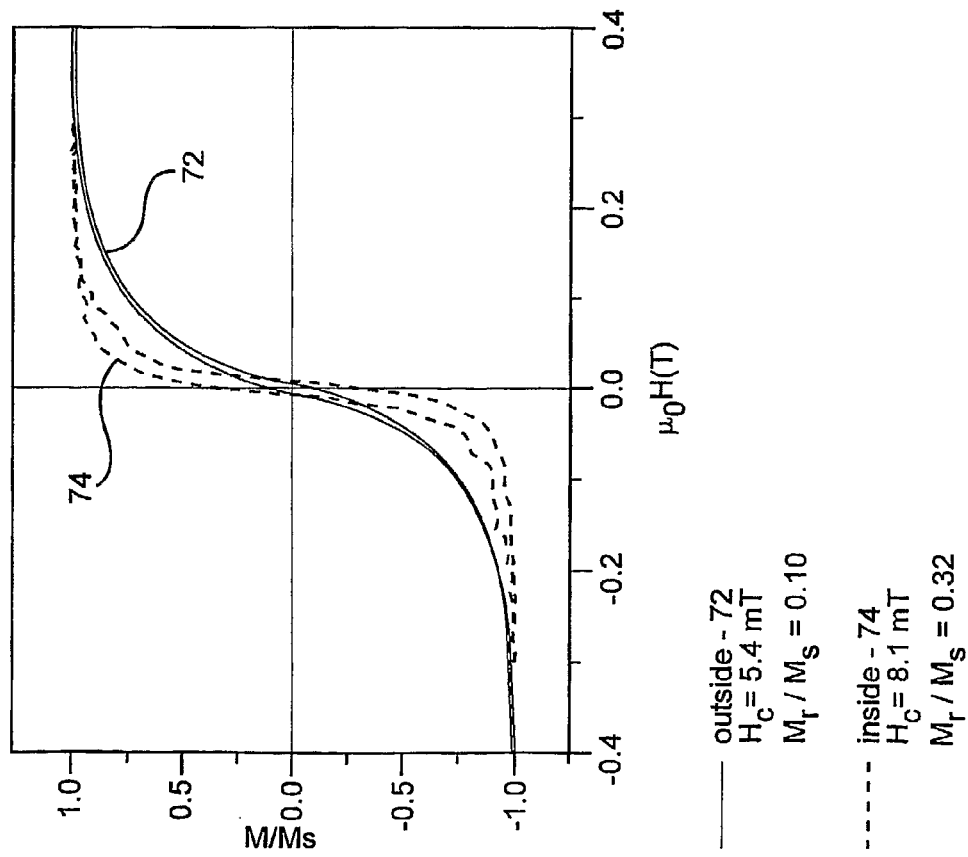
FIG. 3B is a magnified plot around the center (0,0) of the plot of 3A.

In comparison, the magnetic behavior of the magnetic nanotube sample incorporating the magnetic nanocrystals only on the inside (as shown in FIG. 2B) gives even larger values of coercivity and squareness ($H_c=8.1$ mT and $M_r/M_s=0.32$), as shown by line 74 in FIG. 3A and FIG. 3B.

The larger $H_c$ and $M_r/M_s$ values which were obtained for the linear chain of nanocrystals assembled only on the interior surfaces of the nanotubes, indicate that the linear chain assembly of nanocrystals could be magnetostatically coupled and hence behave as a magnetic nanowire rather than individual particles. This simple bio-nanotechnological approach, therefore, allows one to synthesize magnetic nanotubes with characteristics not able to be obtained in nanotubes fabricated by ordinary synthetic means.

What is claimed is:

1. A method of fabricating a magnetic nanotube comprising the steps of:
   providing a plurality of bacterial magnetic nanocrystals, each of the plurality of bacterial magnetic nanocrystals having an outer layer;
   providing at least one nanotube having an interior surface and an exterior surface, the at least one nanotube being able to absorb bacterial magnetic nanocrystals; and
   contacting at least one surface of the at least one nanotube with at least a portion of the plurality of bacterial magnetic nanocrystals, wherein the nanotube is a peptide bolaamphiphile nanotube.

2. The method according to claim 1, wherein the step of providing the at least one nanotube comprises the step of producing the at least one nanotube by self-assembly of a peptide bolaamphiphile.

3. The method according to claim 1, the step of providing the plurality of bacterial magnetic nanocrystals further comprising the step of synthesizing the bacterial magnetic nanocrystals by growing magnetic bacteria anaerobically, and the step of extracting the plurality of bacterial magnetic nanocrystals, wherein the step of extracting comprises:
   disrupting harvested cells;
   collecting the plurality of bacterial magnetic nanocrystals in a column with a magnet; and
   removing a supernatant formed within the column; the supernatant comprising a suspension of the bacterial magnetic nanocrystals.

4. The method according to claim 3, wherein the bacteria are chosen from the group comprising *Magnetospirillum magnetotacticum* MS-1, *Magnetospirillum gryphiswaldense*, and *Magnetospirillum magneticum* AMB-1.

5. The method according to claim 2, wherein the peptide bolaamphiphile comprises bis(N-alpha-amido-glycylglycine)-1,7-heptane dicarboxylate.

6. The method according to claim 1, the step of contacting comprising:
   forming a nanotube solution comprising the at least one nanotube;
   forming a nanocrystal solution comprising a buffer and a concentration of the plurality of bacterial magnetic nanocrystals;
   optimizing the concentration of the plurality of bacterial magnetic nanocrystals in the nanocrystal solution;
   mixing the nanocrystal solution and the nanotube solution; and
   incubating the nanocrystal solution with the nanotube solution until the at least the portion of the plurality of bacterial nanotubes is substantially contacted on the at least one surface of the at least one nanotube.

7. The method according to claim 6, wherein the step of incubating comprises substantially selectively incorporating the at least the portion of the plurality of bacterial magnetic nanocrystals on the interior surface of the at least one nanotube, and further wherein the step of optimizing comprises the step of diluting the concentration of bacterial magnetic nanocrystals to an optimal concentration, the optimal concentration being characterized by the at least the portion of the plurality of bacterial magnetic nanocrystals being substantially incorporated on the interior surface of the at least one nanotube and substantially none of the plurality of nanocrystals being contacted on the exterior surface.

8. The method according to claim 7, wherein the optimal concentration results in a ratio in the mixing step of nanocrystals to nanotubes substantially in a range of about 27 to about 56 nanocrystals to nanotubes.

9. The method according to claim 6, wherein the at least the portion of the plurality of bacterial magnetic nanocrystals is substantially immobilized on at least the exterior surface of the at least one nanotube, and wherein the optimal concentration results in a ratio in the mixing step of nanocrystals to nanotubes substantially in a range of about 550 to about 2800 nanocrystals to nanotubes.

10. The method according to claim 6, wherein the buffer is characterized by a pH substantially in the range of about pH 5 to about pH 9.

11. The method according to claim 7, wherein the at least the portion of the plurality of bacterial magnetic nanocrystals being substantially incorporated on the interior surface of the at least one nanotube align to form a linear chain on the interior surface of the at least one nanotube.

12. A magnetic nanotube comprising:
a plurality of bacterial magnetic nanocrystals, each of the plurality of bacterial magnetic nanocrystals comprising an outer layer;
a nanotube having an interior surface and an exterior surface, the nanotube being able to absorb the bacterial magnetic nanocrystals, wherein the nanotube is a peptide bolaamphiphile nanotube;
wherein the plurality of bacterial magnetic nanocrystals are contacted on at least one of the interior and the exterior surface of the nanotube.

13. The magnetic nanotube of claim 12, wherein the at least one of the interior and the exterior surface is the interior surface, and wherein the plurality of bacterial magnetic nanocrystals is substantially aligned to form a linear chain on the interior surface of the nanotube.

14. The magnetic nanotube of claim 12, wherein the outer layer comprises proteins, further wherein the nanotube comprises peptides, and wherein the outer layer of the plurality of the bacterial magnetic nanocrystals binds with the peptides.

15. The magnetic nanotube of claim 12, wherein the plurality of bacterial magnetic nanocrystals are synthesized by bacteria selected from the group comprising *Magnetospirillum magnetotacticum* MS-1, *Magnetospirillum gryphiswaldense*, and *Magnetospirillum magneticum* AMB-1.

16. The magnetic nanotube of claim 12, wherein each of the plurality of bacterial magnetic nanocrystals is substantially spherical and has an average diameter substantially in a range of about 50 to about 100 nanometers.

17. The magnetic nanotube of claim 12, wherein the bacterial magnetic nanocrystals comprise at least one of magnetite ($Fe_3O_4$) and greigite ($Fe_3S_4$).

18. The magnetic nanotube of claim 12 used as a magnetic nanowire.

19. The magnetic nanotube of claim 12, the magnetic nanotube being characterized as ferromagnetic, and exhibiting a magnetic field of at least 4 mT.

20. The magnetic nanotube of claim 12, wherein the magnetic nanotube is used in one of a cell separation system, a biological assay system, and an enzyme recovery system.

21. The magnetic nanotube of claim 12, wherein the magnetic nanotube is used in cell manipulation.

22. The magnetic nanotube of claim 12, further comprising at least one of a biological material chosen from the group comprising a peptide, a second protein, an enzyme, an antibody, a cell, a DNA, a gene, a virus, a bacteria, a pathogen, and a membrane, the at least one of the biological material attaching to at least one of the interior and the exterior surface of the nanotube.

23. The magnetic nanotube of claim 22, wherein the biological material comprises the cell, the cell being a diseased cell, wherein the magnetic nanotube is used in cell manipulation, and further wherein a magnetic probe is used to separate the diseased cell from a plurality of healthy cells.

24. The magnetic nanotube of claim 12, further comprising one of a drug and a gene attached to one of the interior and the exterior surface, wherein the magnetic nanotube is used in one of a drug delivery system and a gene delivery system, wherein a magnetic field guides the one of the drug and the gene to a desired location.

25. The magnetic nanotube of claim 12, wherein the magnetic nanotube is used in a magnetic resonance imaging system.

* * * * *